United States Patent
Boomgaarden et al.

(10) Patent No.: US 7,056,016 B2
(45) Date of Patent: Jun. 6, 2006

(54) X-RAY SOURCE SUPPORT ASSEMBLY

(75) Inventors: Jonathan C. Boomgaarden, Waukesha, WI (US); Andrew S. Argersinger, Colgate, WI (US)

(73) Assignee: General Electric Company, Schnectady, NY (US)

( * ) Notice: Subject to any disclaimer, the term of this patent is extended or adjusted under 35 U.S.C. 154(b) by 110 days.

(21) Appl. No.: 10/707,597

(22) Filed: Dec. 23, 2003

(65) Prior Publication Data

US 2005/0135565 A1 Jun. 23, 2005

(51) Int. Cl.
*H05G 1/02* (2006.01)

(52) U.S. Cl. .................... 378/193; 378/197

(58) Field of Classification Search ............ 378/193, 378/195–198
See application file for complete search history.

(56) References Cited

U.S. PATENT DOCUMENTS

| | | | |
|---|---|---|---|
| 4,082,955 A * | 4/1978 | Sell ................ 378/196 |
| 4,187,442 A | 2/1980 | Hueschen et al. |
| 4,276,493 A | 6/1981 | Srinivasa et al. |
| 4,501,011 A * | 2/1985 | Hauck et al. ........... 378/196 |
| 4,641,334 A | 2/1987 | Devine, Jr. |
| 4,645,121 A | 2/1987 | Devine, Jr. |
| 4,689,810 A | 8/1987 | Devine, Jr. |
| 4,700,882 A | 10/1987 | Devine, Jr. |
| 4,715,055 A | 12/1987 | Devine, Jr. |
| 4,777,643 A | 10/1988 | Devine, Jr. |
| 4,991,194 A | 2/1991 | Laurent et al. |
| 5,010,563 A | 4/1991 | Laurent et al. |
| 5,140,624 A | 8/1992 | Chrisien |
| 5,548,628 A | 8/1996 | Eggleston et al. |
| 5,550,889 A | 8/1996 | Gard et al. |
| 5,577,093 A | 11/1996 | Benz et al. |
| 5,636,259 A * | 6/1997 | Khutoryansky et al. .... 378/197 |
| 5,784,435 A | 7/1998 | Figurski |
| 5,838,762 A | 11/1998 | Ganin et al. |
| 5,875,227 A | 2/1999 | Bhatt |
| 5,875,228 A | 2/1999 | Truszkowska |
| 6,095,684 A | 8/2000 | Sribar et al. |
| 6,125,168 A | 9/2000 | Bhatt |

(Continued)

OTHER PUBLICATIONS

Stock Drive Products, "Handbook of Gears: Precision & Commercial Inch & Metric" Sterling Instrument/Divisons of Designatronics, Inc., Catalog 190, 1992, p T1, T21, T22 and T61-T69.*

*Primary Examiner*—Craig E. Church
*Assistant Examiner*—Krysytna Suchecki
(74) *Attorney, Agent, or Firm*—Peter Vogel

(57) ABSTRACT

An x-ray generating assembly is provided comprising an x-ray source assembly mounted to a mounting element. The assembly further includes a support assembly comprising a motor element and a gear assembly in communication with the motor element. An output shaft is in communication with the gear assembly such that the output shaft rotates in response to the motor element. The mounting element is positioned around the output shaft. An electromechanical lock is engaged to the mounting element such that the electromechanical lock rotates in concert with the mounting element. The electromechanical lock has an engaged condition and a disengaged condition. The electromechanical lock engages the mounting element when the electromechanical lock is in the engaged condition such that the mounting element rotates with the output shaft. The mounting element is free to rotate when the electromechanical lock is in the disengaged condition.

20 Claims, 2 Drawing Sheets

U.S. PATENT DOCUMENTS

| | | |
|---|---|---|
| 6,181,765 B1 | 1/2001 | Sribar et al. |
| 6,256,375 B1 | 7/2001 | Lu et al. |
| 6,356,619 B1 | 3/2002 | Nagy et al. |
| 6,880,691 B1 * | 4/2005 | Simmons ................... 378/198 |
| 6,928,142 B1 * | 8/2005 | Shao et al. .................. 378/63 |

* cited by examiner

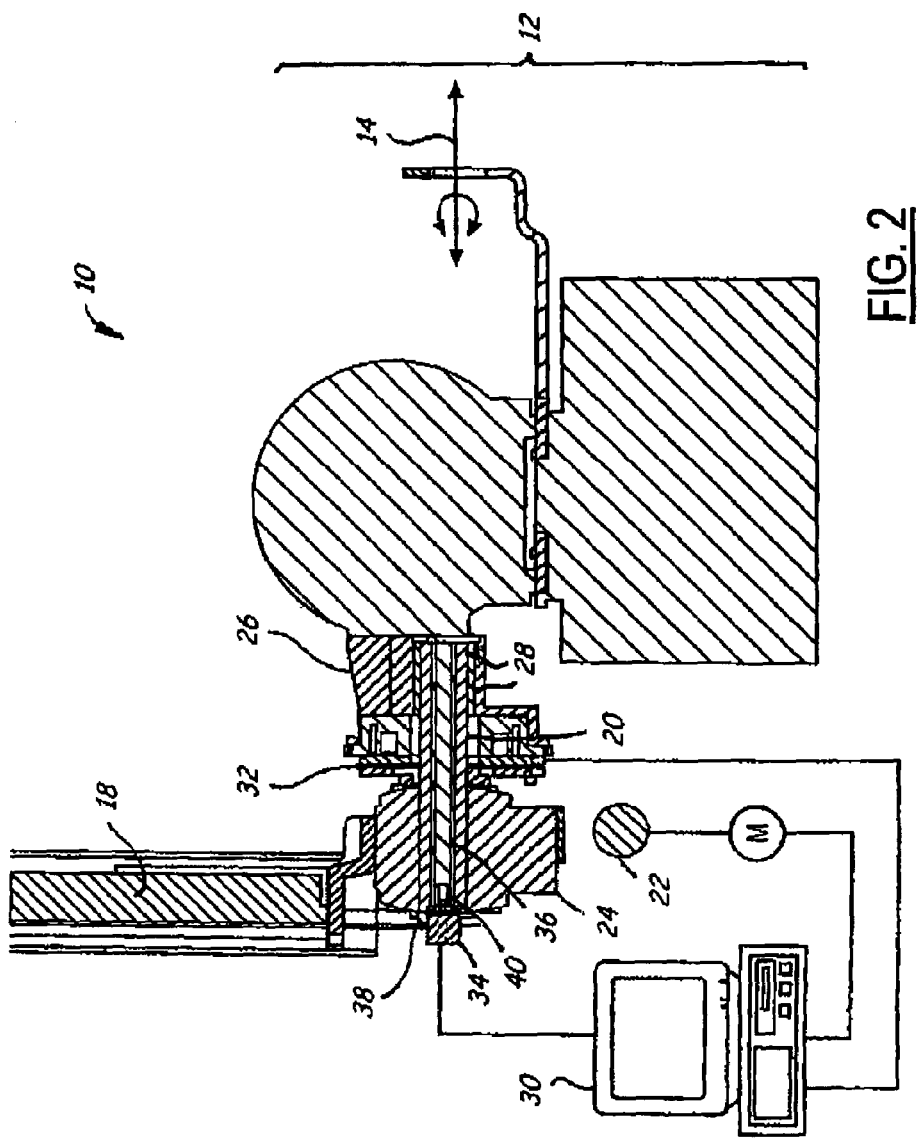

X-RAY SOURCE SUPPORT ASSEMBLY

BACKGROUND OF INVENTION

The present invention relates generally to an x-ray source support assembly, and, more particularly to an x-ray source support assembly with improved profile and control.

X-ray based imaging has been utilized for a wide variety of imaging applications. One such category of applications is comprised of medical imaging. Although it is known that x-ray imaging may take on a wide variety of configurations within the medical industry, it commonly is based on the transmission of low energy rays through a body structure. These low energy rays are subsequently received and processed to formulate an image, often three-dimensional, of the body structure that can by analyzed by clinicians as a diagnostic aid.

For many x-ray imaging applications the position and of the x-ray source assembly and the direction of the x-ray streams must be positioned properly to facilitate proper imaging. In these applications, it is common for the x-ray source to be pivoted about an axis to provide the proper emission direction. In addition, many imaging applications require automated positioning of the x-ray source. This is commonly accomplished through the use of a motorized assembly engaging the rotational axis by way of a clutch assembly. Separate clutch and braking assemblies further increase the profile of many existing assemblies. Existing motorized assemblies are commonly bulky, complicated, and expensive. In addition, their size and unwieldy nature often interferes with the supporting structure necessary to support the x-ray source assembly. This results in the requirement that the rotational axis by offset to one side of the supporting structure. By offsetting the rotational axis, motion of the x-ray source can become more complex and require additional controls and assemblies. This additional complexity can serve to increase the cost and hamper the functionality of the resultant imaging assembly.

It would, therefore, be highly desirable to have an x-ray source support assembly that provided a compact positioning support with improved functionality. Furthermore, it would be highly desirable to have an x-ray source support assembly that eliminated the need for separate clutch and braking assemblies.

SUMMARY OF INVENTION

An x-ray generating assembly is provided comprising an x-ray source assembly mounted to a mounting element. The assembly further includes a support assembly comprising a motor element and a gear assembly in communication with the motor element. An output shaft is in communication with the gear assembly such that the output shaft rotates in response to the motor element. The mounting element is positioned around the output shaft. An electromechanical lock is engaged to the output shaft such that the electromechanical lock rotates in concert with the output shaft. The electromechanical lock has an engaged condition and a disengaged condition. The electromechanical lock engages the mounting element when the electromechanical lock is in the engaged condition such that the mounting element rotates with the output shaft. The mounting element is free to rotate when the electromechanical lock is in the disengaged condition.

Other features of the present invention will become apparent when viewed in light of the detailed description of the preferred embodiment when taken in conjunction with the attached drawings and appended claims.

BRIEF DESCRIPTION OF DRAWINGS

FIG. 2 is a cross-sectional illustration of the x-ray generating assembly illustrated in FIG. 1, the cross-section taken along the lines 2—2 in the direction of the arrows.

DETAILED DESCRIPTION

Figure 1:
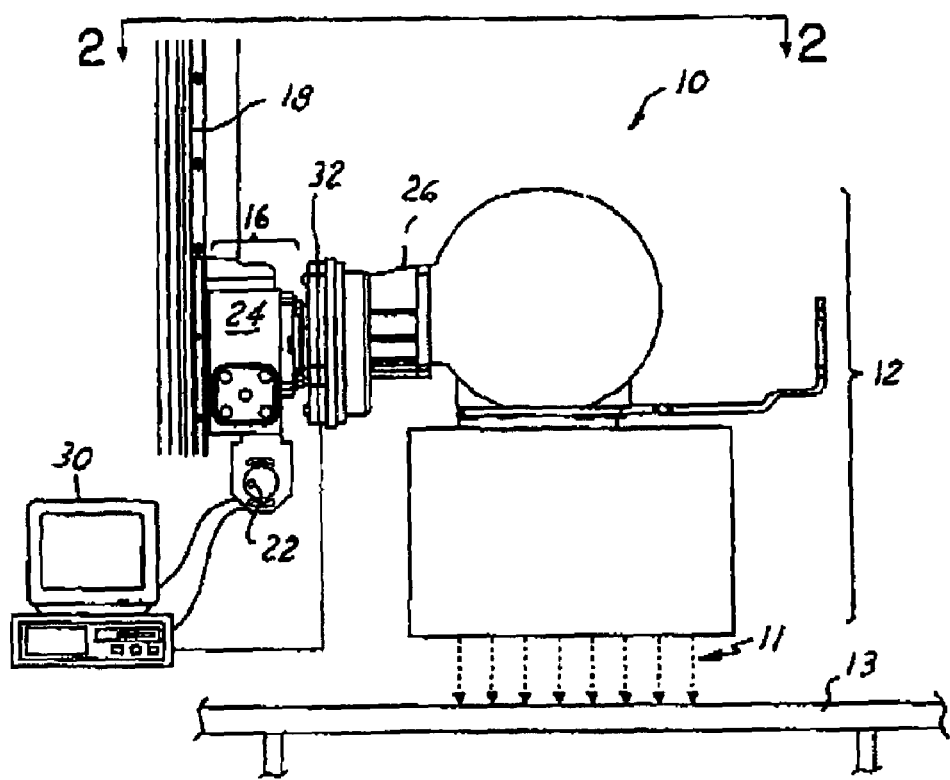
FIG. 1 is an illustration x-ray generating assembly for use in the present invention.

Referring now to FIGS. 1–2, which are illustrations of an x-ray generating assembly 10 in accordance with the present invention. The x-ray generating assembly 10 is intended for use in a wide variety of imaging applications. The x-ray generating assembly 10 includes an x-ray source assembly 12 rotatable about a rotation axis 14. Although the rotation axis 14 is illustrated as a horizontal axis, a wide variety of rotational axis 14 are contemplated by the present invention. The x-ray source assembly 12 generates a beam of x-rays 11 directed at an object or table 13. The x-ray source assembly 12 is suspended from a support assembly 16, which in turn is mounted to a support structure 18. The support assembly 16 preferably acts as the primary structural support for the x-ray source assembly 12.

An output shaft 20 acts as the primary horizontal element of the support assembly 16 supporting the x-ray source assembly 12. A motor element 22 is in communication with the output shaft 20 by way of a gear assembly 24 positioned between the motor element 22 and the output shaft 20. Although a variety of motor elements 22, gear assemblies 24, and output shafts 20 are contemplated, the gear assembly 24 is preferably a worm gear assembly and the output shaft 20 is preferably a worm-driven output shaft. The gear assembly 24 is additionally preferably non-reversible i.e. resistant to being back driven. In this case the output shaft 20 cannot be used to drive the motor element 22. This factor allows the x-ray source assembly 12 to be effectively locked in place when coupled to the output shaft 20 without the need for an additional locking element. In this fashion the profile of the x-ray generating assembly 10 can be reduced and the output shaft 20 can support the x-ray source assembly 12 directly on the rotation axis 14. Although a wide variety of non-reversible gear assemblies 24 are contemplated, one embodiment contemplates the use of a high reduction worm gear assembly 24. The high reduction worm gear assembly 24 allows the motor element to drive the output shaft 20 while effectively preventing the output shaft 20 from driving the gear assembly 24. It should be understood, however, that the present invention further contemplates the use of non-locking gear boxes wherein position can be held by motor and motor controls. In addition, at least one embodiment is contemplated wherein the gear assembly 24 is self locking in a static condition but may be slightly back-drivable when moving.

The x-ray source assembly 12 is fixedly attached to a mounting element 26 and is preferably supported on the output shaft 20 by way of a mounting element 26. The mounting element 26 is positioned around the output shaft 20 and engages the output shaft 20 by way of a bearing assembly 28 positioned around the output shaft 20. In this way the mounting element 26 is free to rotate about the output shaft 20. The present invention, however, desires the x-ray source assembly 12 to be rotatably coupled to the output shaft 20 such that, when desired, the output shaft 20 can control the position of the x-ray source assembly 12. A controller 30, such as a computer, in communication with the motor element 22 can provide such control. In order to controllably couple/de-couple the x-ray source assembly 12 to the output shaft 20, the present invention includes an electromechanical lock 32 assembly. The electromechanical lock 32 is in permanent communication with the mounting element 26 such that it rotates with the mounting element 26. The electromechanical lock 32 has an engaged condition and a disengaged condition. When in the engaged condition, the electromechanical lock 32 engages the output shaft 20 and thereby couples the output shaft 20 to the x-ray source assembly 12. When in the disengaged condition, the electromechanical lock 32 disengages the output shaft 20 and the mounting element 26 and x-ray source assembly 12 are free to rotate about the output shaft 20 such that they can be manually positioned. Although a specific mechanical embodiment has been described, it should be understood that the primary function of the electromechanical lock 32 is to provide a controllable coupling between the output shaft 20 and the x-ray source assembly 12.

Additionally, it is contemplated that the electromechanical lock 32 can be activated by energizing the lock assembly. The functioning of electromechanical locks is well known in the art. Although a wide degree of variations are contemplated, one embodiment contemplates the energizing of the electromechanical lock 32 to cause the lock 32 to disengage the output shaft 20. In this fashion, the default condition of the x-ray generating assembly 10, with the electromechanical lock 32 de-energized, is such that the x-ray source assembly 12 is coupled to the output shaft 20. Although the electromechanical lock 32 may be controlled in a wide variety of fashion, many as simple as a switch, one embodiment contemplates the electromechanical lock 32 to be in communication with the controller 30 such that automated engagement/disengagement can be controlled.

It is understood that since the x-ray source assembly 12 can be rotated about the rotational axis 14 in both a free manner and a output shaft 20 coupled manner, automated control of the x-ray source assembly 12 by the controller 30 would be complicated without knowledge of the position of the x-ray source assembly 12 at all times. The present invention, therefore, further contemplates the use of a feedback device 34 in communication with both the support assembly 16 and the x-ray source assembly 12. The feedback device 34, therefore, registers the relative rotational position of the x-ray source assembly 12 to the support assembly 16 even after free rotation. By placing the feedback device 34 in communication with the controller 30, an automated positioning system can properly compensate for manual repositioning of the x-ray source assembly 12. A wide variety of feedback devices 34 may be utilized including, but not limited to, potentiometers, optical encoders, absolute encoders, virtual absolute encoders, or other position measuring devices.

It is contemplated that the feedback device 34 can be placed in communication with the support assembly 16 and the x-ray source assembly 12 in a variety of fashions. In keeping with the reduce profile nature of the present invention, however, one embodiment contemplates the use of a hollow output shaft 20. A source positioning shaft 36 is positioned within said hollow output shaft 20 and is permanently coupled to the x-ray source assembly 12. In this fashion, the source positioning shaft 36 rotates with the x-ray source assembly 12 even when the x-ray source assembly 12 is disengaged from the output shaft 20. By placing the feedback device 34 in communication with the shaft end 40 of the source positioning shaft 36, the rotation of the shaft can be measured. Additionally, by positioning the feedback device 34 in a position adjacent the shaft end 40 the feedback device 34 can be incorporated without interfering with the profile of the x-ray generating assembly 10.

While particular embodiments of the invention have been shown and described, numerous variations and alternative embodiments will occur to those skilled in the art. Accordingly, it is intended that the invention be limited only in terms of the appended claims.

The invention claimed is:

1. An x-ray generating assembly comprising:
    an x-ray source assembly mounted to a mounting element;
    a support assembly comprising:
    a motor element;
    a gear assembly in communication with said motor element; and
    an output shaft in communication with said gear assembly such that said output shaft rotates in response to said motor element, said mounting element positioned around said output shaft; and
    an electromechanical lock engaged to said mounting element such that said electromechanical lock rotates in concert with said mounting element, said electromechanical lock having an engaged condition and a disengaged condition, said electromechanical lock engaging said output shaft when said electromechanical lock is in said engaged condition such that said mounting element rotates with said output shaft, said mounting element free to rotate about said output shaft to any relative rotational position when said electromechanical lock is in said disengaged condition, said electromechanical lock engaging in said relative rotational position.

2. An x-ray generating assembly as described in claim 1, wherein said electromechanical lock moves from said engaged condition to said disengaged condition when said electromechanical lock becomes energized.

3. An x-ray generating assembly as described in claim 1, wherein said gear assembly comprises a high reduction worm gear assembly.

4. An x-ray generating assembly as described in claim 1, wherein said gear assembly includes a back-drive force greater than a locking force of said electromechanical lock.

5. An x-ray generating assembly as described in claim 1, wherein said x-ray source is suspended from a supporting structure by said output shaft.

6. An x-ray generating assembly as described in claim 1, further comprising:
    a controller in communication wit said motor element, said controller including logic adapted to control the position of said x-ray source assembly.

7. An x-ray generating assembly as described in claim 1, wherein said output shaft comprises a hollow output shaft.

8. An x-ray generating assembly as described in claim 7, further comprising:
    a source positioning shaft positioned within said output shaft, said source positioning shaft engaged to said x-ray source assembly such that said source positioning shaft rotates with said x-ray source assembly at all times including in said disengaged condition.

9. An x-ray generating assembly as described in claim 8, further comprising:
    a feedback device in communication with both said source positioning shaft and said support assembly such that the position of said x-ray source assembly can be determined at all times to determine said relative rotational position.

10. An x-ray generating assembly as described in claim 9, wherein said feedback device is an optical encoder.

11. An x-ray generating assembly as described in claim 9, wherein said feedback device is in communication with said controller.

12. An x-ray generating assembly comprising:
an x-ray source assembly mounted to a mounting element;
a primary structural support assembly supporting said x-ray source assembly comprising:
a motor element;
a gear assembly in communication with said motor element; and
an output shaft coupled wit said gear assembly such that said output shaft rotates in response to said motor element; and
an electromechanical lock having an engaged condition and a disengaged condition, said x-ray source assembly engaged to said output shaft when said electromechanical lock is in said engaged condition, said x-ray source assembly free to rotate about said output shaft to any relative rotational position when said electromechanical lock is in said disengaged condition, said electromechanical lock engaging in said relative rotational position.

13. An x-ray generating assembly as described in claim 12, wherein said gear assembly comprises a high reduction worm gear assembly axially aligned with said output shaft and said electromechanical lock.

14. An x-ray generating assembly as described in claim 12, wherein said gear assembly includes a back-drive force greater than a locking force of said electromechanical lock.

15. An x-ray generating assembly as described in claim 12, further comprising:
a controller in communication with said motor element, said controller including logic adapted to control the position of said x-ray source assembly.

16. An x-ray generating assembly as described in claim 12, further comprising:
a feedback device in communication with both said primary structural support assembly and said x-ray source assembly such that the relative position of said x-ray source assembly can be determined at all times including in said disengaged condition.

17. An x-ray generating assembly as described in claim 12, further comprising:
a source positioning shaft positioned within said output shaft, said source positioning shaft engaged to said x-ray source assembly such that said source positioning shaft rotates with said x-ray source assembly at all times, said output shaft comprises a hollow output shaft; and
a feedback device in communication with both said source positioning shaft and said primary structural support assembly such that the position of said x-ray source assembly can be determined at all times to determine said relative rotational position.

18. A method of positioning an x-ray source assembly comprising:
supporting the x-ray source assembly on a support assembly including an output shaft, said output shaft in communication with a motor element;
communicating rotational movement from said motor element to said output shaft by means of a worm gear assembly in communication with said motor element and said output shaft;
engaging an electromechanical lock whereby the x-ray source assembly is coupled to said output shaft; and
disengaging said electromechanical lock such that the x-ray source assembly is free to rotate about said output shaft to any relative rotational position; and
engaging said electromechanical lock in said relative rotational position.

19. A method of positioning an x-ray source assembly as described in claim 18, further comprising:
monitoring the rotational position of the x-ray source assembly using a feedback device in communication with both the x-ray source assembly and said support assembly.

20. A method of positioning an x-ray source assembly as described in claim 19, further comprising:
using a controller to automate movement of the x-ray source assembly, said controller in communication with said motor element, said electromechanical lock, and said feedback device.

* * * * *